United States Patent [19]
Newman et al.

[11] 3,978,205
[45] Aug. 31, 1976

[54] DENTIFRICE INCLUDING LUSTER IMPARTING AGENT

[75] Inventors: Peter John Newman, Maidenhead; Charles Andrew Watson, Ruislip, both of England

[73] Assignee: Lever Brothers Company, New York, N.Y.

[22] Filed: Mar. 29, 1974

[21] Appl. No.: 456,331

[30] Foreign Application Priority Data
Apr. 11, 1973   United Kingdom............... 17291/73

[52] U.S. Cl.................................. 424/49; 424/154; 424/357
[51] Int. Cl.².......................................... A61K 7/16
[58] Field of Search .............. 424/49, 69, 154, 155, 424/357

[56] References Cited
UNITED STATES PATENTS

| | | | |
|---|---|---|---|
| 2,994,642 | 8/1961 | Bossard................. | 424/49 |
| 3,608,067 | 9/1971 | Irani...................... | 424/49 |
| 3,705,940 | 12/1972 | Kirchgassner......... | 424/49 |

OTHER PUBLICATIONS

Kirk–Othmer's Ency. of Chem. Tech. 2nd Ed., vol. 18, 1969, pp. 62–72.

Primary Examiner—James O. Thomas, Jr.
Assistant Examiner—A. P. Fagelson
Attorney, Agent, or Firm—James J. Farrell; Kenneth F. Dusyn; Melvin H. Kurtz

[57] ABSTRACT

Dentifrices containing an abrasive cleaning agent and a luster agent impart an enhanced luster to the teeth through the use as luster agent of fumed silica obtained by vapourising and recondensing silica.

2 Claims, No Drawings

DENTIFRICE INCLUDING LUSTER IMPARTING AGENT

This invention relates to dentifrices.

Dentifrices almost invariably contain an abrasive cleaning agent for the removal of adherent deposits on teeth. Usually the particles of the abrasive have an average particle size within the range of about 5 to about 25 microns. Examples of those abrasives which find or have found extensive commercial usage are silica xerogels, hydrated alumina, calcium carbonate, dicalcium phosphate (anhydrous and the dihydrate), insoluble sodium metaphosphate and calcium pyrophosphate.

It is desirable that after tooth cleaning the teeth should have a shiny lustrous appearance. To this end it has been proposed to include in dentifrices a more finely-divided mineral specifically to act as a tooth polishing agent. For example, in U.S. Pat. No. 3,060,098 Linde Type A alpha-alumina has been proposed for this purpose.

We have now found that a material which is particularly effective for enhancing the lustre of teeth is a fumed silica obtained by vapourising and recondensing silica.

Accordingly the present invention provides a dentifrice comprising an abrasive cleaning agent and a lustre agent, wherein the lustre agent is a fumed silica obtained by vapourising and recondensing silica.

The fumed silica used in this invention can be made by a high temperature arc process in which silica is used as part of the electrodes, although a plasma generator can also be used as the heat source for the vapourisation. This form of fumed silica is to be contrasted with the more well-known form obtained by the flame-hydrolysis process in which silicon tetrachloride is reacted with hydrogen and oxygen in a flame to form a very fine silica. The latter form of fumed silica has been shown to be inferior as a lustre agent to the fumed silica used in the dentifrices of the invention and which is obtained by the vapourisation of silica.

Fume silica made by the flame-hydrolysis process (e.g. the material sold under the name AEROSIL) is well-known as an ingredient of toothpastes in which it is included as a thickening agent. The vapourised silica used in the process of this invention differs in a number of ways from flame-hydrolysis silica. In particular the silica used in the present invention is chemically very inert (being dehydroxylated) whereas flame-hydrolysis silicas because of the presence of hydroxyl groups at the surface of the particles are not inert, and they can react with various organic compounds to effect replacement of the hydroxyl groups by organic groups and in this way a hydrophobic silica can be produced. Furthermore, the hydroxyl groups present at the surface of the flame-hydrolysed silicas lead to the particles linking themselves together due to hydrogen bonding forming chains and a three-dimensional structure and this formation is primarily responsible for the silica's thickening effect on various liquid systems. In contrast, the silicas used in this invention are substantially dehydroxylated and consequently have substantially less thickening power.

The silica used in the present invention is produced as substantially spherical particles of size about 10 to about 100 millimicrons which form aggregates. The material is substantially anhydrous and non-porous and, as explained, relatively inert.

The amount of the lustre-producing silica incorporated in dentifrices may vary from about 0.1 to about 40% by weight, although the amount used will usually be relatively small, for instance between about 0.5 and 10% by weight.

The lustre-producing silica used in this invention may be included in a wide variety of dentifrice compositions. These may be powder or liquid products but they are preferably the better known paste products extrudable from collapsible tubes or dispensed from aerosol containers. Extrudable toothpastes include the visually clear gel-like products recently introduced onto the market.

Toothpastes usually contain from about 5 to about 60 percent by weight of abrasive cleaning agent. The liquid phase usually comprises a mixture of water and a humectant, such as glycerol, sorbitol or propylene glycol 400 or mixtures thereof. Various other ingredients in minor amounts are conventional, particularly surface-active agent, thickener or binder and flavouring agent. Other ingredients which might also be included are anti-bacterial agents, for example 1,6-di-(p-chlorophenyl biguanido) hexane and its non-toxic acid addition salts, preservatives, sweetening agents, chloroform and titanium dioxide.

Experiments have been performed demonstrating the superior lustre-producing properties of dentifrices in accordance with the invention. The standard dentifrice used in these experiments had the following composition.

| | Weight % |
|---|---|
| Alumina trihydrate (aps 16 to 21 microns) | 54.0 |
| Sorbitol syrup (70%) | 27.0 |
| Sodium carboxymethylcellulose | 0.8 |
| Sodium lauryl sulphate | 2.0 |
| Saccharin | 0.2 |
| Flavour | 1.0 |
| Dicalcium phosphate dihydrate | 1.0 |
| Water | to 100.0 |

(aps = average particle size)

The test dentifrices used were the same as the standard product except that they contained additionally a lustre agent in place of a part of the water. Details of the various lustre agents tested are given in Table 1.

TABLE 1

| Test Dentifrice | Lustre Agent Amount | Nature |
|---|---|---|
| A | 1% | Spherical particles of amorphous substantially anhydrous and non-porous silica predominantly of particle size about 40 millimicrons obtained by the vapourisation and condensation of silica |
| B | 2% | Flux calcined diatomite |
| C | 1% | Alpha-alumina (aps 3 microns) |
| D | 2% | Precipitated silica (aps 8 microns) |
| E | 2% | Flame-hydrolysis silica |
| F | 2% | Titanium dioxide |
| G | 2.5% | Alpha-alumina (aps 0.3 micron)-Linde A |

The comparison of the lustre-producing properties of the dentifrices was carried out using a procedure which involved the measurement by means of a modified Sargrove Dental Reflectometer of the specular component of the light reflected from the surface of a tooth, previously dulled by brushing with a slurry of chalk, which had been brushed with the toothpaste under test. For each dentifrice, including the standard, there was determined the rate of change of the lustre of the tooth surface between 0 and 3,000 brush strokes. The ratio between the rate value obtained with a test product and the standard product is termed the Lustre Value for the test product. The Lustre Values obtained for the dentifrices A to G are given below in Table 2.

TABLE 2

| Test Dentifrice | Lustre Value |
| --- | --- |
| A | 4.1 |
| B | 2.7 |
| C | 2.1 |
| D | 1.5 |
| E | 1.0 |
| F | 0.9 |
| G | 0.5 |

The experiment showed that the test product A was clearly superior to the other test products and the standard product.

The degree of scratching produced by the test dentifrices was also determined. This was done by mechanically brushing previously polished extracted teeth for 15,000 brush strokes with a test dentifrice. The surface was then examined at a 1,000 magnification using a scanning electron microscope and the degree of scratching rated on a 1 to 4 scale, thus:

1 for unmarked surfaces
2 for slightly marked
3 for appreciably scratched
4 for severely scratched The results are given in Table 3 below.

TABLE 3

| Test Dentifrice | Scratch Rating |
| --- | --- |
| A | 1 |
| B | 3 |
| C | 4 |
| D | 2 |
| E | 1 |
| F | 3 |
| G | 4 |

This experiment showed that the test dentifrice A, as well as producing the highest degree of lustre, also resulted in a very low degree of scratching.

What is claimed is:

1. A toothpaste composition comprising in said toothpaste, by weight, from 5 to about 60 percent of an abrasive cleaning agent having an average particle size of about 5 to about 25 microns, and 0.1 to about 40 percent of a finely divided lustre agent, said lustre agent consisting of substantially dehydroxylated fumed silica, having been vapourized and recondensed in the form of spherical particles of a size of from about 10 to about 100 millimicrons.

2. A method of cleaning and imparting a lustre to teeth which comprises brushing said teeth with a sufficient amount, to impart said lustre, of the toothpaste composition of claim 1.

* * * * *